United States Patent
Westphal et al.

(10) Patent No.: US 9,155,813 B2
(45) Date of Patent: Oct. 13, 2015

(54) VOLATILE MATERIAL DISPENSING SYSTEM AND METHOD OF USE

(71) Applicant: S.C. Johnson & Son, Inc., Racine, WI (US)

(72) Inventors: Nathan R. Westphal, Union Grove, WI (US); Jerome A. Matter, Racine, WI (US); Deliang Shi, Kenosha, WI (US); Jonathan N. Mandell, Gurnee, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 189 days.

(21) Appl. No.: 14/080,462

(22) Filed: Nov. 14, 2013

(65) Prior Publication Data

US 2015/0130089 A1    May 14, 2015

(51) Int. Cl.
  *B01F 3/04* (2006.01)
  *A61L 9/12* (2006.01)
  *A01M 1/20* (2006.01)

(52) U.S. Cl.
  CPC ............ *A61L 9/122* (2013.01); *A01M 1/2027* (2013.01); *A01M 1/2033* (2013.01); *A61L 9/12* (2013.01); *B01F 3/04* (2013.01); *B01F 3/04241* (2013.01); *B01F 2215/009* (2013.01)

(58) Field of Classification Search
  CPC ..... B01F 3/04; B01F 3/04007; B01F 3/04241
  USPC ............... 261/83, 84, 101, 102, 105, DIG. 88
  See application file for complete search history.

(56) References Cited

U.S. PATENT DOCUMENTS

| | | | |
|---|---|---|---|
| 5,480,591 A | 1/1996 | Lagneaux et al. | |
| 5,695,692 A | 12/1997 | Kennedy | |
| 5,851,442 A * | 12/1998 | Spector | 261/30 |
| 6,080,367 A | 6/2000 | Lin | |
| 6,179,275 B1 | 1/2001 | Lagneaux et al. | |
| 6,425,530 B1 | 7/2002 | Coakley | |
| 7,718,119 B2 | 5/2010 | Tajima et al. | |
| 7,793,861 B2 | 9/2010 | Bankers et al. | |
| 8,043,569 B2 | 10/2011 | Tranzeat | |
| 8,480,248 B2 | 7/2013 | Demarest et al. | |
| 2003/0044326 A1 | 3/2003 | Yamasaki et al. | |
| 2004/0180070 A1 | 9/2004 | Inoue et al. | |
| 2005/0220664 A1 | 10/2005 | Hitzler et al. | |
| 2005/0285538 A1 | 12/2005 | Jaworski et al. | |
| 2007/0140923 A1 | 6/2007 | Wiegand | |
| 2010/0140372 A1 | 6/2010 | Patrick | |
| 2011/0290908 A1 | 12/2011 | Tranzeat et al. | |
| 2012/0275932 A1 | 11/2012 | Sharma | |

OTHER PUBLICATIONS

PCT/US2014/064977 International Search Report and Written Opinion dated May 27, 2015.

* cited by examiner

*Primary Examiner* — Robert A Hopkins

(57) ABSTRACT

A dispensing system includes a refill having a reservoir for containing a volatile material. A permeable membrane is disposed over the reservoir and allows the volatile material to be released therethrough. The dispensing system also includes a housing adapted to retain the refill and a manual drive mechanism, which is in communication with the refill. Actuation of the manual drive mechanism causes the refill to rotate more than 180° about a longitudinal axis.

20 Claims, 17 Drawing Sheets

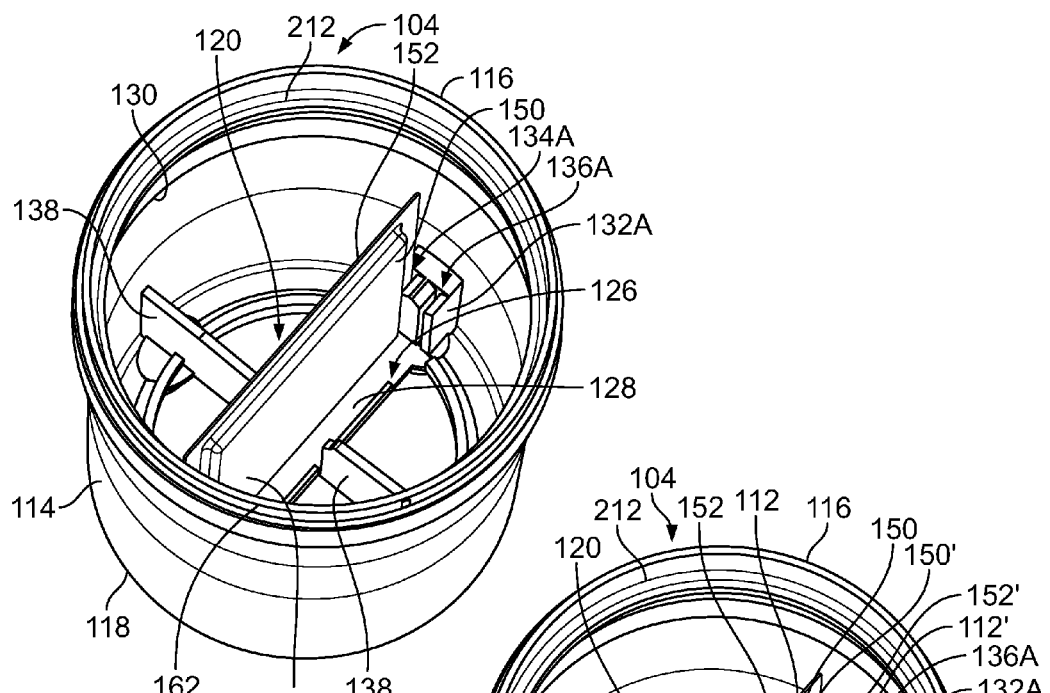
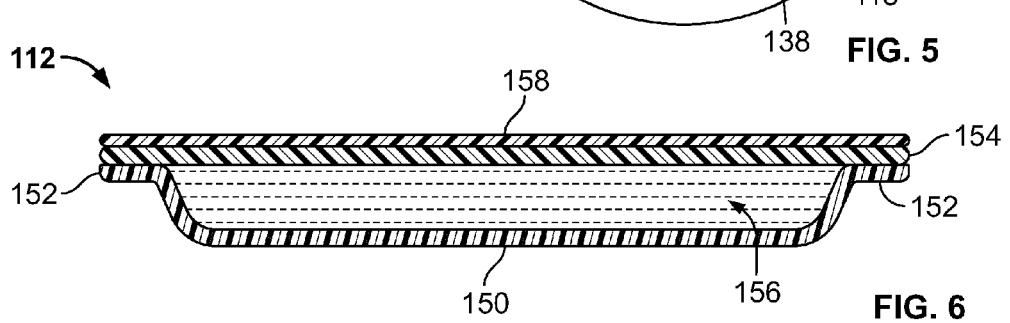

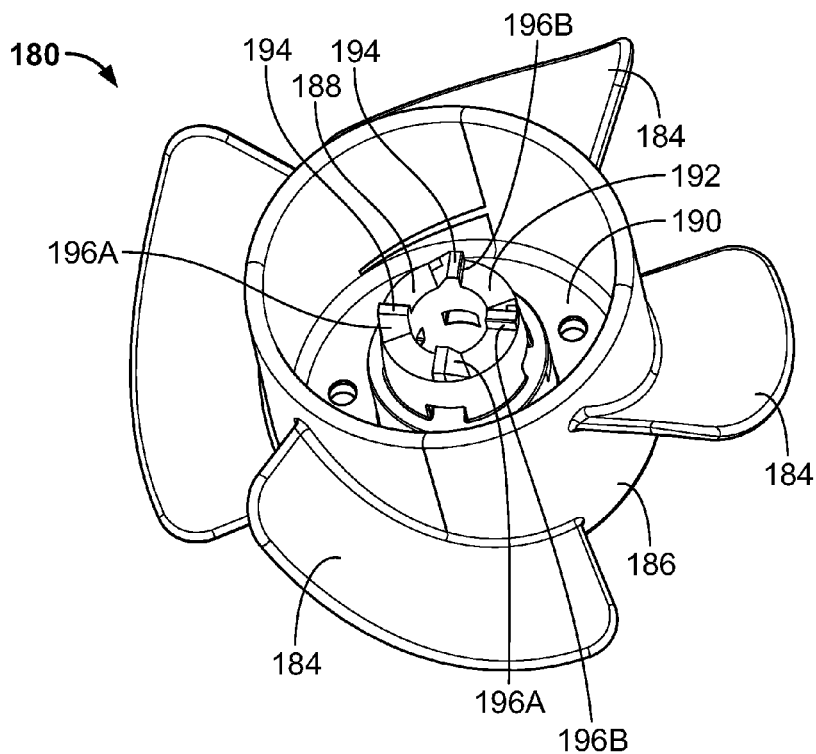
FIG. 10
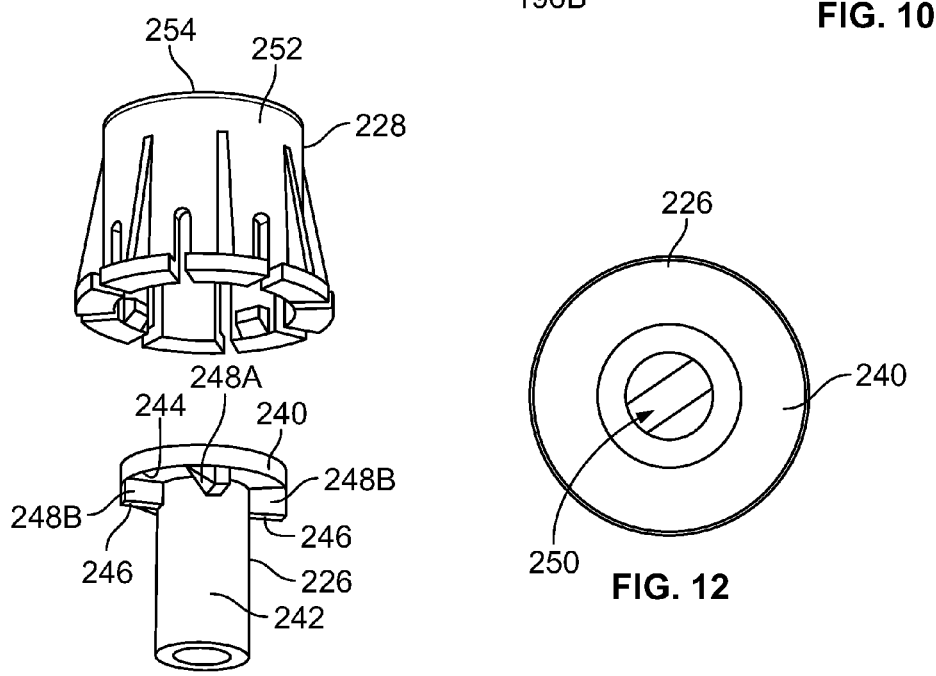
FIG. 11
FIG. 12

VOLATILE MATERIAL DISPENSING SYSTEM AND METHOD OF USE

REFERENCE REGARDING FEDERALLY SPONSORED RESEARCH OR DEVELOPMENT

Not applicable

SEQUENTIAL LISTING

Not applicable

BACKGROUND OF THE DISCLOSURE

1. Field of the Disclosure

The present invention is directed to a volatile material dispensing system and, in particular, a volatile material dispenser which is adapted to release a volatile material into an environment during use both passively and actively.

2. Description of the Background of the Disclosure

Many devices and apparatuses have been developed for delivering a volatile material to an environment of use. Some devices disseminate the volatile material using passive means. Examples of devices with passive means include devices having a volatile material evaporate from a substrate or membrane, which disseminate the volatile material into the environment. Other passive devices have a reservoir, which contains a volatile material that is released into the environment as the volatile material evaporates. However, these devices do not allow a user to provide an increased dissemination of the volatile material into the environment.

In addition to the aforementioned passive devices, active devices or devices that include a combination of passive and active devices, have been developed to aid in the dissemination of the volatile material. Many of these active dispensers require the use of electrical components to run a fan, heater, or other mechanism to enhance the dissemination of the volatile material from a substrate, membrane, or reservoir.

Therefore, there is a need in the art for an improved apparatus for manually enhancing delivery of a volatile material without the aid of an electrical component.

SUMMARY OF THE INVENTION

According to one embodiment, a dispensing system includes a refill having a reservoir for containing a volatile material therein. A permeable membrane is disposed over the reservoir and allows the volatile material to be released therethrough. The dispensing system also includes a housing adapted to retain the refill and a manual drive mechanism, which is in communication with the refill. Actuation of the manual drive mechanism causes the refill to rotate more than 180° about a longitudinal axis.

According to another embodiment, a dispensing system includes a fan and a refill having a reservoir with a volatile material disposed therein. A permeable membrane covers the reservoir such that the volatile material is released through the permeable substrate in a first passive state. Rotation of the fan causes air to pass over the permeable membrane to release the volatile material in a second active state. The volatile material is released radially about a full 360° of the dispensing system.

According to a different embodiment, a dispensing system includes a non-electric spring-activated drive mechanism and a refill having a reservoir containing a volatile material therein. The volatile material is released from the refill in a first passive state, and the drive mechanism causes the refill to rotate more than 180° about a longitudinal axis of the dispensing system.

The above and other aspects of the present invention will be apparent from the following description of the preferred embodiments of the invention and from the accompanying drawings.

BRIEF DESCRIPTION OF THE DRAWINGS

FIG. 4 is an isometric view of the base of FIG. 3 having a refill disposed therein;

FIG. 5 is an isometric view of the base of FIG. 3 having two refills disposed therein;

FIG. 6 is a cross sectional view of the refill taken along the line 6-6 of FIG. 1;

FIG. 10 is an isometric view of a fan for use in the dispensing system of FIG. 1;

FIG. 11 is an exploded isometric view of a portion of a drive mechanism of the dispensing system of FIG. 1;

FIG. 12 is a plan view of a ratchet for use in the dispensing system of FIG. 1;

DETAILED DESCRIPTION OF THE DRAWINGS

Figure 1:
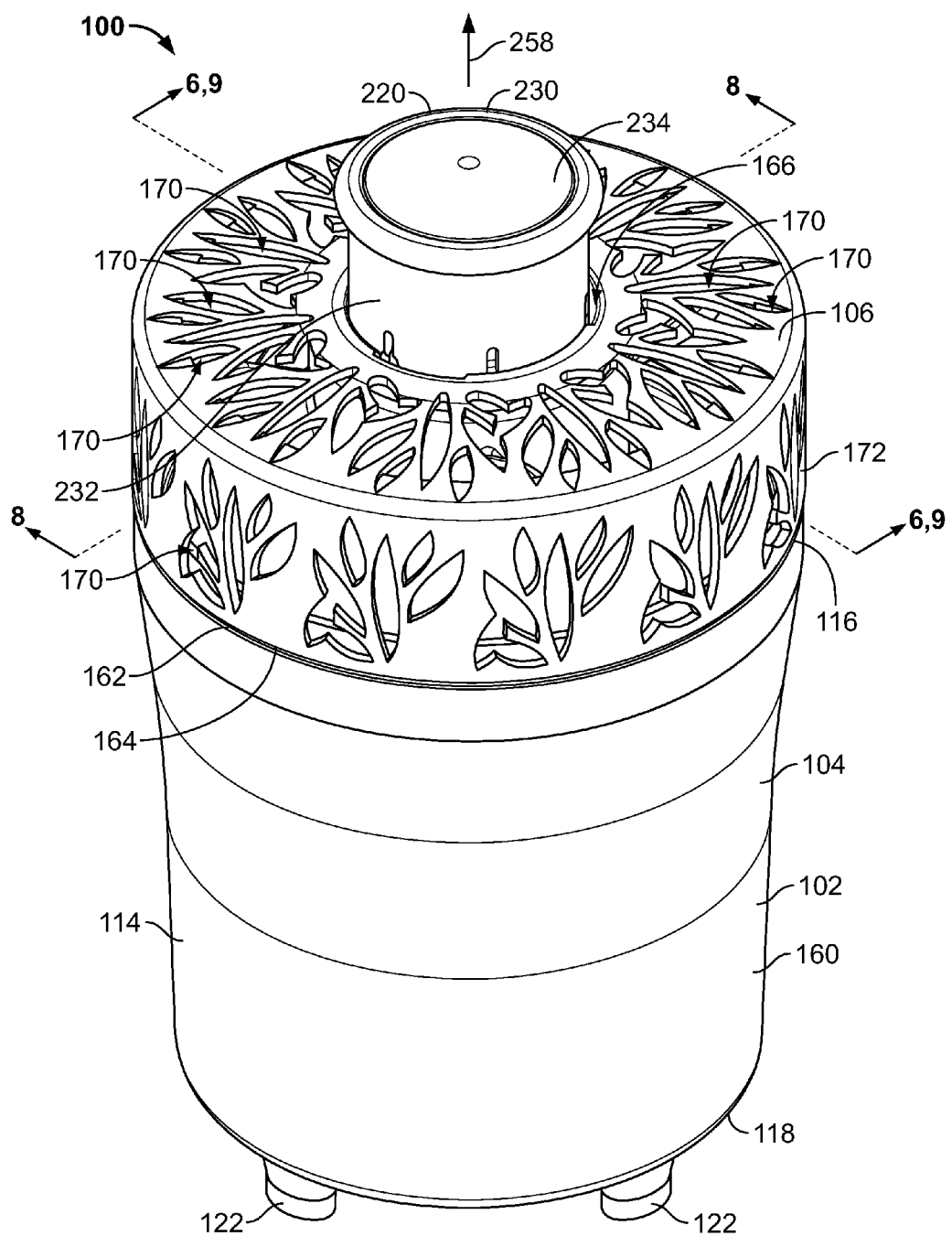
FIG. 1 is an isometric view of a dispensing system.
Figure 2:
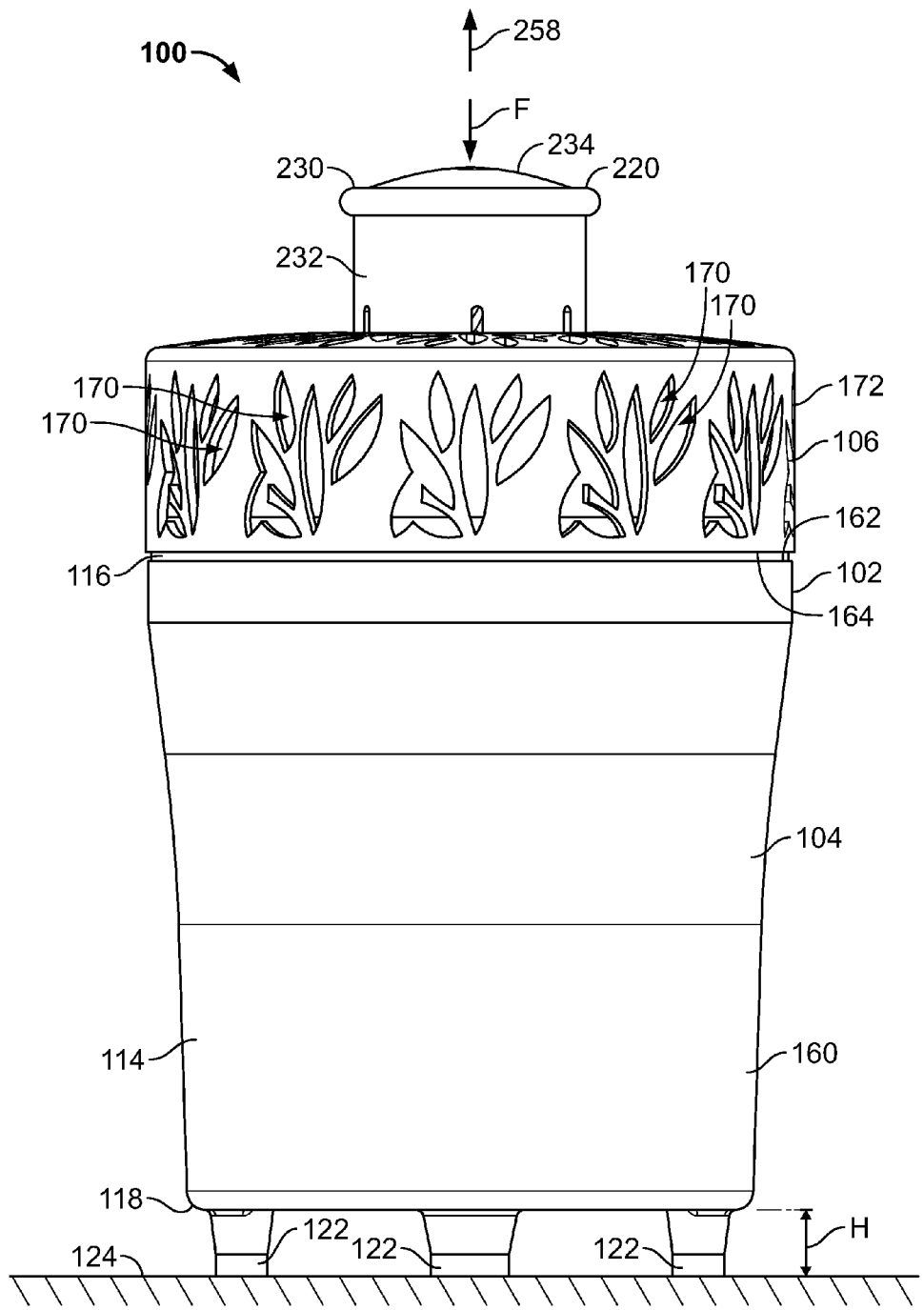
FIG. 2 is a front elevational view of the dispensing system of FIG. 1.
Figure 3:
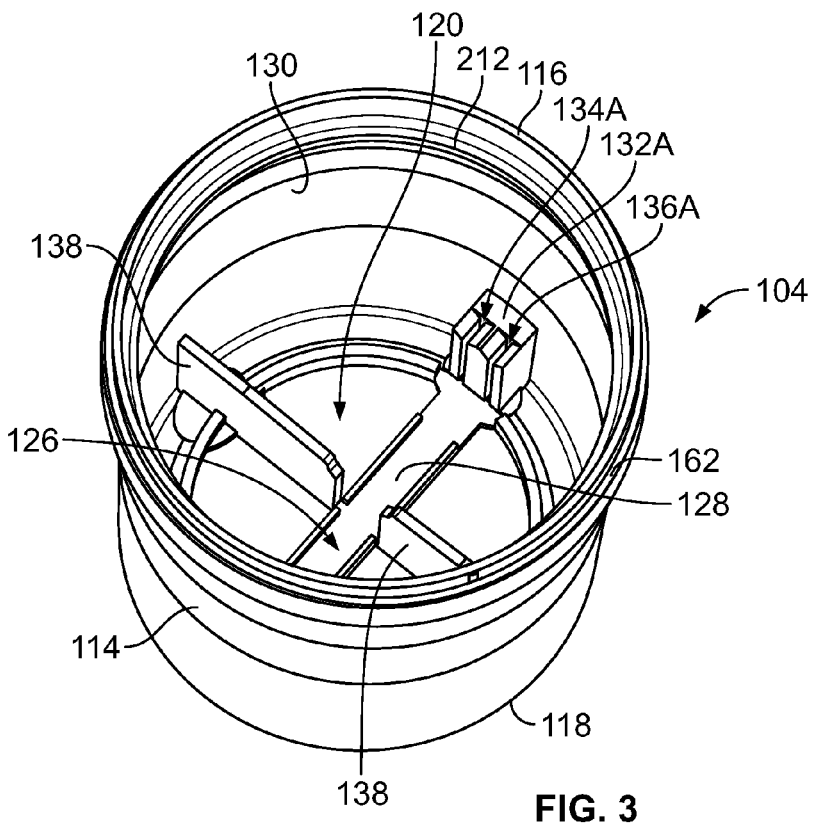
FIG. 3 is an isometric view of a base of the dispensing system of FIG. 1.
Figure 3A:
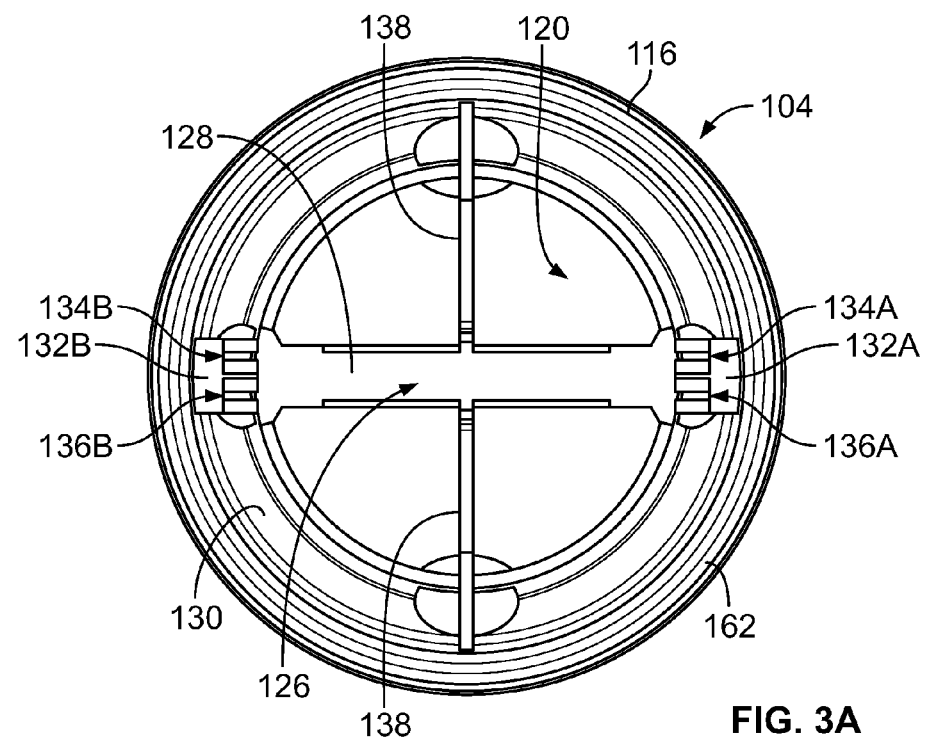
FIG. 3A is a plan view of the base of FIG. 3.

Referring to FIGS. 1-12, a volatile material dispensing system 100 includes a housing 102 comprising a base 104 and a cover 106. A fan assembly 108, a manual drive mechanism 110, and at least one refill 112 are disposed within the housing 102.

With reference to FIGS. 1-3A, the base 104 is generally cylindrical shaped and includes a sidewall 114 extending from an open top end 116 to a bottom end 118 thereof. An aperture 120 is disposed in the bottom end 118. A plurality of feet 122 are also provided on the bottom end 118 of the base 104. The feet 122 rest on a support surface 124 and retain the bottom end 118 of the base 104 a distance H from the support surface 124, thereby allowing airflow through the aperture 120, which will be described in greater detail below. Alternatively, the feet 122 may be omitted so that the bottom end 118 rests on the support surface 124, and the aperture 120 may be disposed in the sidewall 114 adjacent the bottom end 118 to allow air to enter the base 104.

Turning now to FIGS. 3-5, 8, and 9, a refill support structure 126 is disposed within the base 104 adjacent the bottom end 118 thereof. The refill support 126 includes a bridge 128 extending from an inner surface 130 of the sidewall 114 over the aperture 120. Two support blocks 132A, 132B are disposed at opposing ends of the bridge 128. Support block 132A includes a pair of slots 134A, 136A, disposed therein, which corresponds with a pair of slots 134B, 136B disposed in the opposing support block 132B. The refill support structure 126 further includes a pair of upstanding walls 138 extending from the inner surface 130 of the sidewall 114 across the aperture 120 substantially perpendicular to the bridge 128.

Referring more particularly to FIG. 6, the refill 112 includes a reservoir 150 and a flange 152 surrounding the reservoir 150. A permeable membrane 154 is adhered to the flange 152 to cover the reservoir 150 and extends across the refill 112. The reservoir 150 is filled with a volatile material 156, which may comprise one or more active ingredients for diffusion into the surrounding atmosphere, such as a fragrance, air freshener, odor eliminator, insecticide, or insect repellant. It is contemplated that any type of volatile material with one or more active ingredients suited for dispersal through the permeable membrane 154 may be used with the refill 112, e.g., an active(s) suspended, mixed, or otherwise formed within a gel, liquid, or thickened liquid. An impermeable laminate 158 is releasably adhered to the refill 112 over the permeable membrane 154 to prevent release of the volatile material 156 prior to use.

In use, as illustrated in FIGS. 3-5, 8, and 9, the refill 112 is inserted into the base 104 through the open top end 116 thereof. The refill 112 is inserted such that the flange 152 slides within the opposing slots 134A, 134B in the support blocks 132A, 132B, respectively. The upstanding walls 138 provide additional support in retaining the refill 112 by preventing substantial movement of the refill 112 in the direction of the reservoir 150 or the permeable membrane 154. In some embodiments a second refill 112' containing the same or different volatile material 156' may be inserted into the base 104. The second refill 112' is inserted such that the flange 152' slides within the opposing slots 136A, 136B in the support blocks 132A, 132B, respectively. When two refills 112, 112' are inserted into the base 104, the refills 112, 112' are inserted such that the permeable membrane 154, 154' of each refill 112, 112' faces outwardly and away from each other. Alternatively, the membranes 154, 154' may be inserted in the same orientation or in a manner that causes the permeable membrane 154, 154' to face one another. For example the refills 112, 112' may be positioned within the base 104 such that the reservoirs 150, 150' are disposed toward the inner surface 130 of the sidewall 114 of the base 104 and the permeable membranes 154, 154' are facing inwardly.

Figure 7:
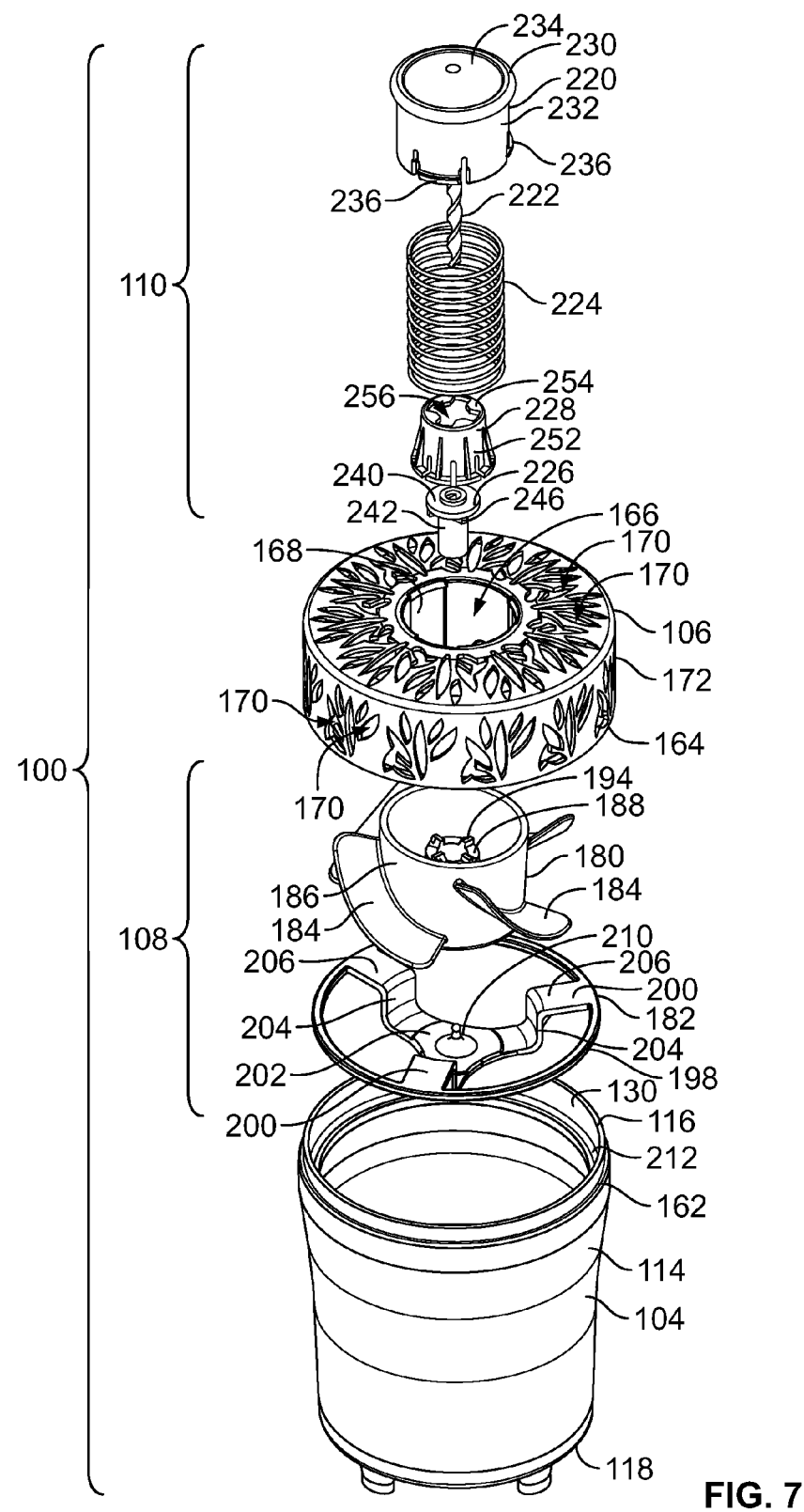
FIG. 7 is an exploded isometric view of the dispensing system of FIG. 1.
Figure 8:
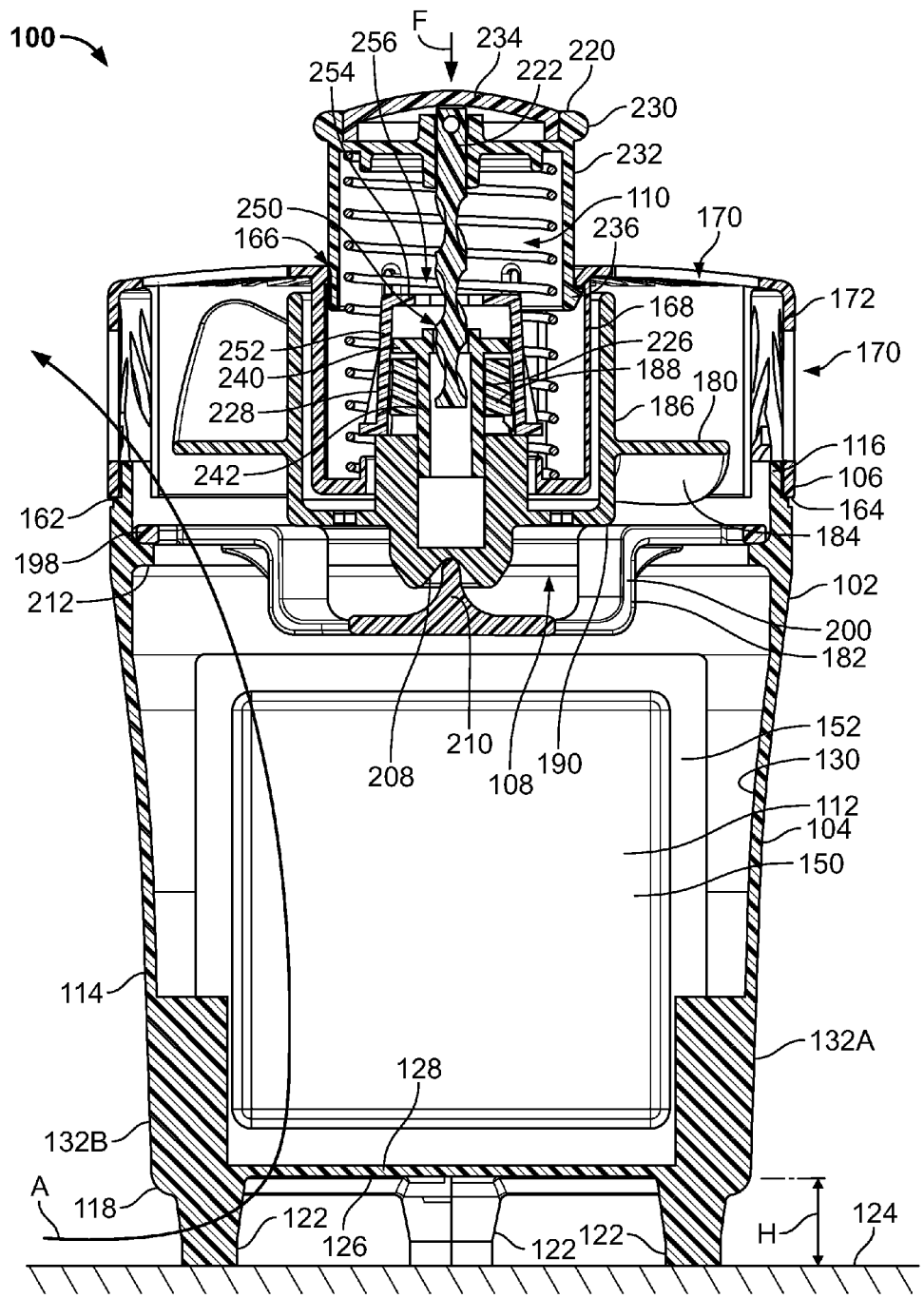
FIG. 8 is a cross-sectional view of the dispensing system of FIG. 1, taken across the line 8-8 of FIG. 1.
Figure 9:
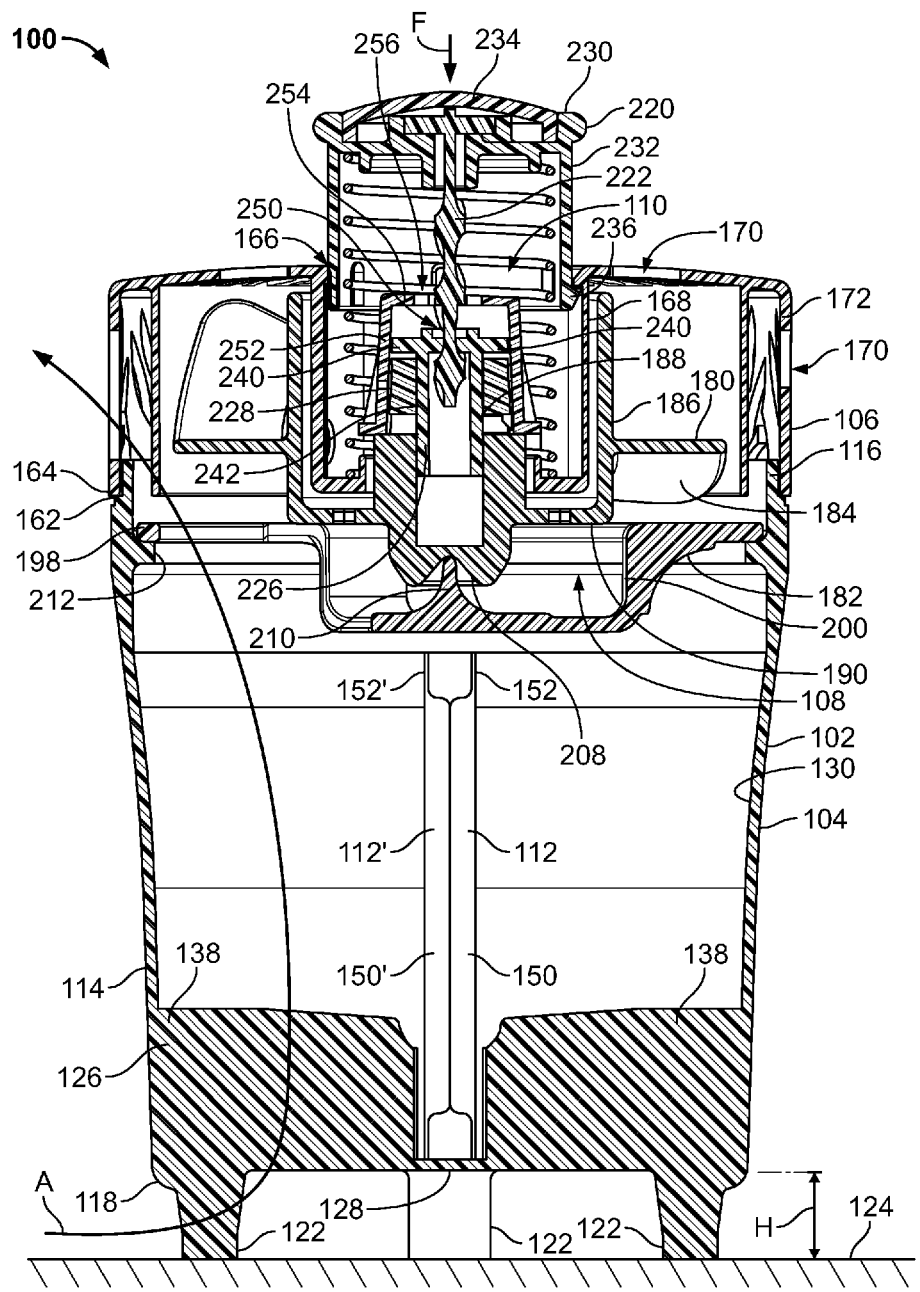
FIG. 9 is a cross-sectional view of the dispensing system of FIG. 1, taken across the line 9-9 of FIG. 1.

With reference to FIGS. 1, 2, 8, and 9, the cover 106 is adapted for interfitting relationship with the base 104. The cover 106 slides over the top end 116 of the sidewall 114 of the base 104 and frictionally engages with an exterior surface 160 thereof, which prevents the cover 106 from releasing from the base 104 or rotating during use. Additionally, a ledge 162 is disposed around the exterior surface 160 of the sidewall 114 to provide added support as a resting surface for a lower edge 164 of the cover 106. Although the cover 106 is shown to be releasably attached to the base 104 via friction fit, it is contemplated that other connection means known to those skilled in the art may also be used to releasably attach the cover 106 to the base 104, e.g., the cover 106 may be snapped onto the base 104 or screwed onto the base 104. FIGS. 7-9 show that the cover 106 also includes an aperture 166 disposed therethrough. A cylindrical support 168 depends from the cover 106 adjacent the aperture 166. The cylindrical support 168 is adapted to help support and retain the fan assembly 108 and manual drive mechanism 110 within the housing 102. Further, a plurality of vents 170 are disposed in top and side portions of a sidewall 172 of the cover 106, which allow air laden with the volatile material 156 to exit the dispensing system 100. In the present embodiment the vents 170 are shown as a decorative leaf-like pattern, however, it is contemplated that the vents 170 may be of any shape and pattern. Further, it is contemplated that larger or smaller vents 170 may be used to increase or decrease the amount of volatile material 156 released.

Turning to FIGS. 7-10, the fan assembly 108 generally includes a fan 180 and a pivot 182. The fan 180 includes a plurality of fan blades 184 extending from a central barrel 186 thereof. The barrel 186 is shaped to receive the cylindrical support 168 of the cover 106 when the dispensing system 100 is assembled. As shown in FIG. 10, the fan 180 further includes a cylindrically shaped axle 188 that is located within the barrel 186 and extends upwardly from a bottom end 190 thereof. An upper end 192 of the axle 188 includes a plurality of teeth 194. The teeth 194 include sloped first sides 196A and vertical second sides 196B.

Referring again to FIGS. 7-9, the pivot 182 includes an outer ring 198 and a plurality of arms 200 extending inwardly from the outer ring 198 to a bottom portion 202 thereof. The arms 200 include main portions 204 that extend upwardly from the bottom portion 202 of the pivot 182 and overhang portions 206 that extend outwardly about 90° from the main portions 204 and connect the main portions 204 to the outer ring 198. Turning to FIGS. 8 and 9, the barrel 186 of the fan 180 is received within the arms 200 of the pivot 182. A groove 208 on the bottom end 190 of the barrel 186 rests on a cone shaped projection 210 extending from the bottom 202 of the pivot 182. The cone-shaped projection 210 acts as a pivot point about which the fan 180 rotates within the dispensing system 100.

Referring still to FIGS. 7-9, the pivot 182 is designed to fit within the top end 116 of the base 104 when the dispensing system 100 is assembled. When assembled, the outer ring 198 of the pivot 182 rests on a ledge 212 disposed on the inner surface 130 of the sidewall 114 of the base 104 adjacent the top end 116 thereof. The outer ring 198 frictionally engages the inner surface 130 of the sidewall 114 to prevent the pivot 198 from rotating when the fan 180 rotates.

Referring now to FIGS. 7-9, 11, and 12, the various components of the manual drive mechanism 110 will be described. The drive mechanism 110 includes a plunger 220, a screw 222, a spring 224, a ratchet 226, and a ratchet cover 228. The plunger 220 comprises a circular top wall 230 and a cylindrical wall 232 depending from the top wall 230. A button insert 234 may also be provided within the top wall 230, or the top wall 230 and button insert 234 may be a single piece. The cylindrical wall 232 of the plunger 220 is shaped to fit within the cylindrical support 168 of the cover 106. Hooks 236 that are disposed on a distal end of the cylindrical wall 232 interact with the cylindrical support 168 to prevent the plunger 220 from being removed from the cover 106 after assembly. The screw 222 is retained within the top wall 232 and extends downwardly therefrom within the cylindrical wall 232.

As shown in FIG. 11, the ratchet 226 includes a disc-shaped cap 240 and a cylindrical tube 242 depending from an underside 244 of the cap 240. A plurality of teeth 246 also depend from the underside 244 of the cap 240. The teeth 246 include sloped first sides 248A and vertical second sides 248B. The teeth 246 on the ratchet 226 are designed to interact with the plurality of teeth 194 on the axle 188 of the fan 180. As shown in FIG. 12, the ratchet 226 further includes a slot 250 within the cap 240, which is shaped to receive the screw 222 therethrough in a screw-type engagement to convert vertical movement of the plunger 220 into rotational movement of the fan 180.

Referring again to FIG. 11, the ratchet cover 228 includes a body 252 having a closed top end 254. The ratchet cover 228 is designed to fit over the ratchet 226 and the axle 188 to retain the ratchet 226 in the housing 102 when the dispensing system 100 is assembled. An aperture 256 is disposed in the top end 254 of the ratchet cover 228 (see FIGS. 7-9), which is designed to allow the screw 222 to pass through the ratchet cover 228 and into the ratchet 226.

To assemble the dispensing system 100 a user removes the impermeable laminate 158 from the refill 112 and then inserts the refill 112 into the base 104. The fan assembly 108, manual drive mechanism 110, and cover 106 are then attached to the base 104. In this passive state, the volatile material 156 evaporates through the permeable membrane 154 of the refill 112 and exits the dispensing system 100 through the plurality of vents 170 in the cover 106.

At any time, a user may activate the dispensing system 100 to release a greater amount of the volatile material 156 by providing a downward force F on the plunger 220. Application of the force F on the plunger 220 causes the screw 222 to move vertically downward through the slot 250 in the ratchet 226, which causes the ratchet 226 to rotate in a first direction. Rotation of the ratchet 226 in the first direction causes the vertical sides 248B of the ratchet teeth 246 to engage with the vertical sides 196B of the axle teeth 194, thereby causing the fan 180 to rotate about a longitudinal axis 258 of the dispensing system 100. The rotating fan 180 draws air into the housing 102 of the dispensing system 100 through the aperture 120 in the bottom end 118 of the base 104 as indicated by arrow A. The air thereafter passes over a surface of the permeable membrane 154 of the refill 112 in a direction substantially parallel to the permeable membrane 154. Forcing the air across the surface of the permeable membrane 154 in a direction substantially parallel to the permeable membrane 154 provides for a more efficient release of air as opposed to air moving in a direction perpendicular to the surface of the permeable membrane 154. The airflow thus encounters less resistance when passing by the refills 112, 112' to provide for an enhanced delivery of the volatile material 156 into the surrounding atmosphere. Subsequent to passing over the permeable membrane 154, the air is laden with the volatile material 156 and exits the housing 102 through the plurality of vents 170 in the top and side portions of the sidewall 172 of the cover 106. In the present embodiment, the air is exhausted from the vents 170 radially about a full 360° of the dispensing system. During this active state, an increased rate and volume of the volatile material 156 is released from the dispensing system 100 as compared to the passive state.

When the downward force F is removed from the plunger 220, the spring 224 biases the plunger 220 upwardly to the unactuated position. The upward movement of the plunger 220 causes upward movement of the screw 222 through the slot 250 in the ratchet 226. This upward movement causes the ratchet 226 to rotate in a second opposite direction. When the ratchet 226 rotates in the second direction, the sloped sides 248A of the ratchet teeth 246 are able to ride up and over the sloped sides 196A of the axle teeth 194, thereby allowing the ratchet 226 to rotate without causing the fan 180 to rotate in the second opposite direction. In some embodiments, momentum created by the rotating fan 180, will cause the fan 180 to continue rotating in the first direction even after the force F on the plunger 220 has been removed.

Referring now to FIGS. 13-19 another embodiment of a volatile material dispensing system 300 is shown, wherein like elements to those in FIGS. 1-12 are given the same numbers. Generally, the dispensing system 300 includes the cover 106, the manual drive mechanism 110, and the refill 112 as described above in combination with an alternative base 304 and fan assembly 308.

Figure 13:
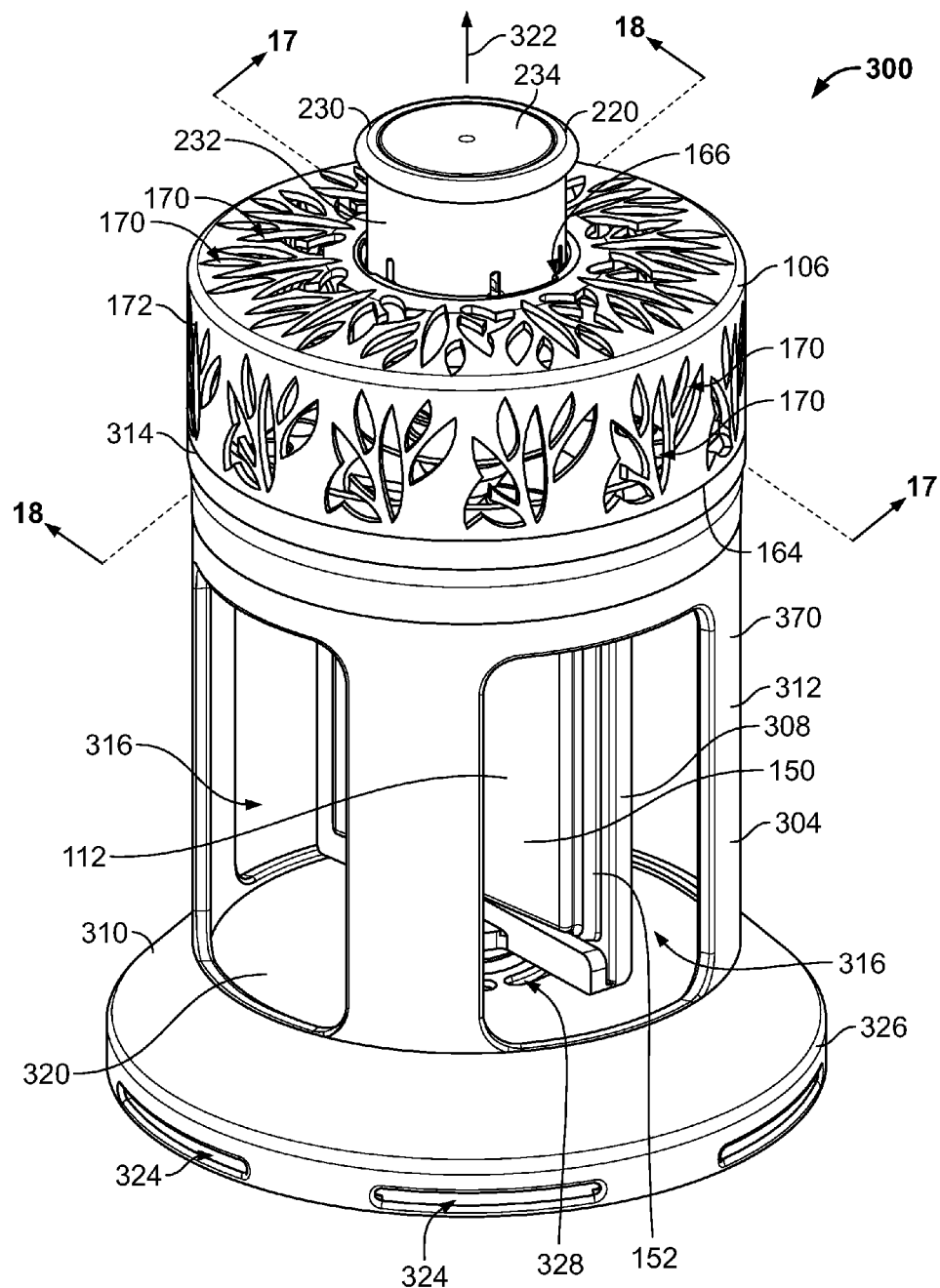
FIG. 13 is an isometric view of a further embodiment of a dispensing system.
Figure 14:
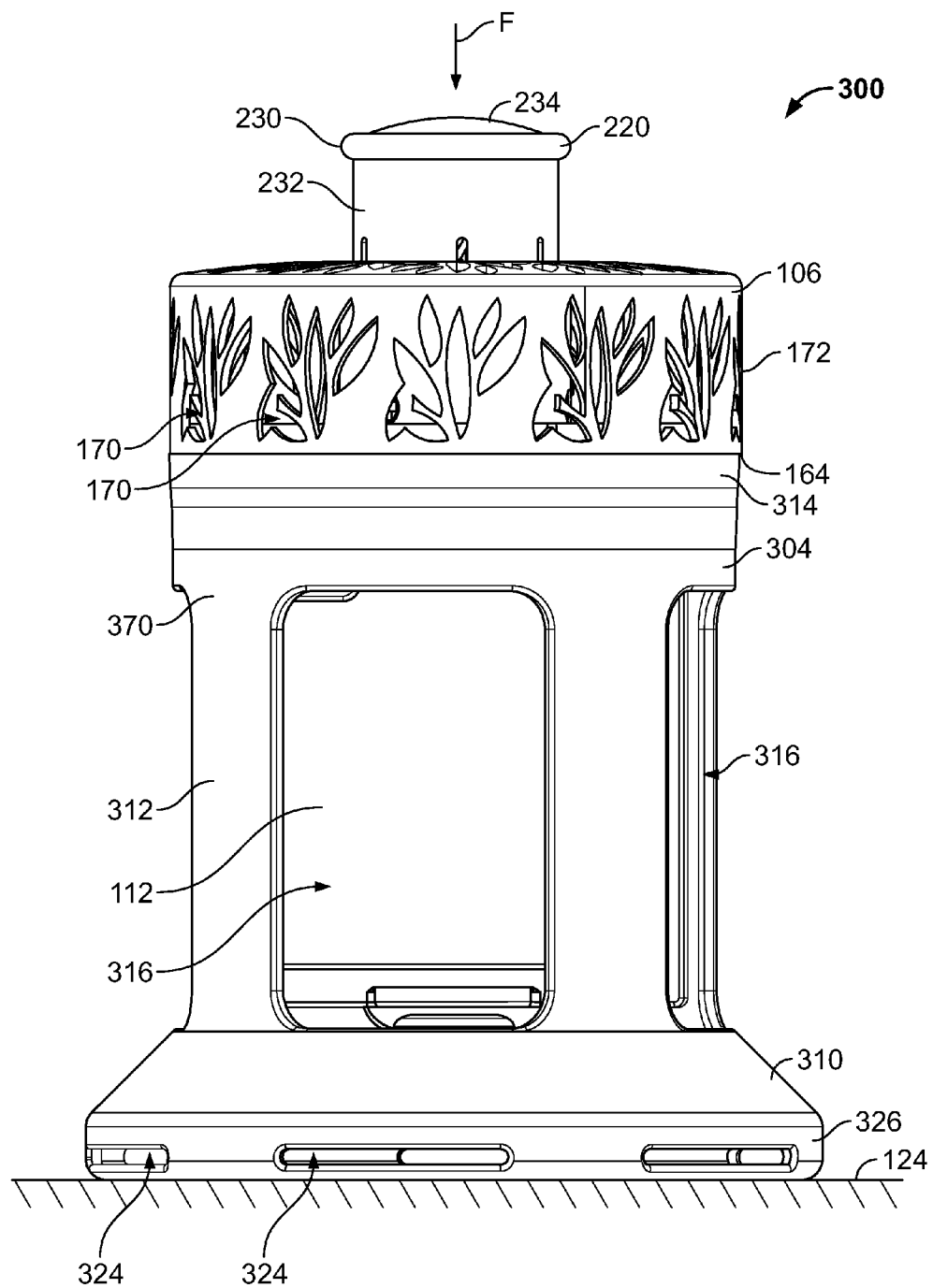
FIG. 14 is front elevational view of the dispensing system of FIG. 13.
Figure 15:
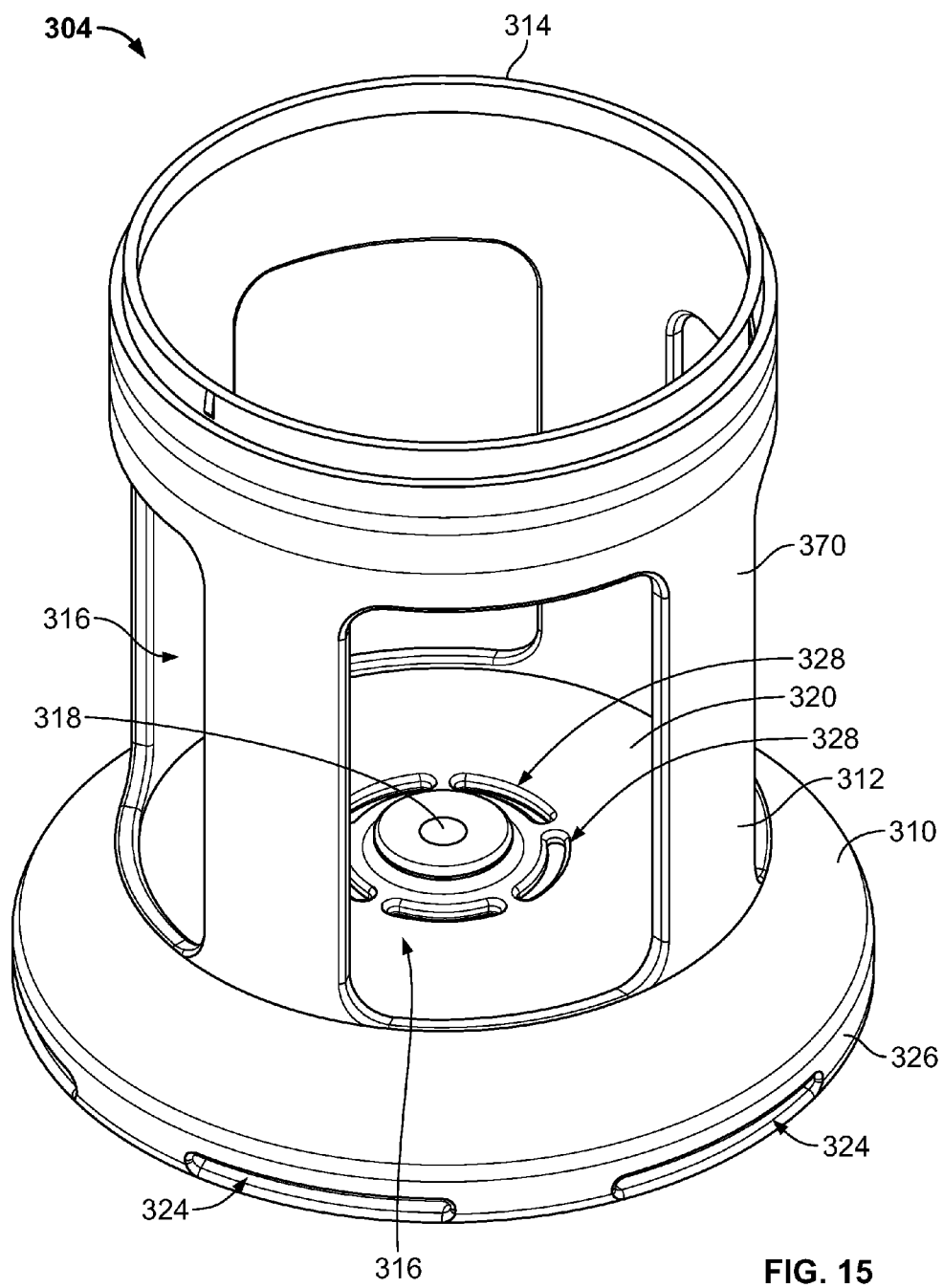
FIG. 15 is an isometric view of a base of the dispensing system of FIG. 13.
Figure 16:
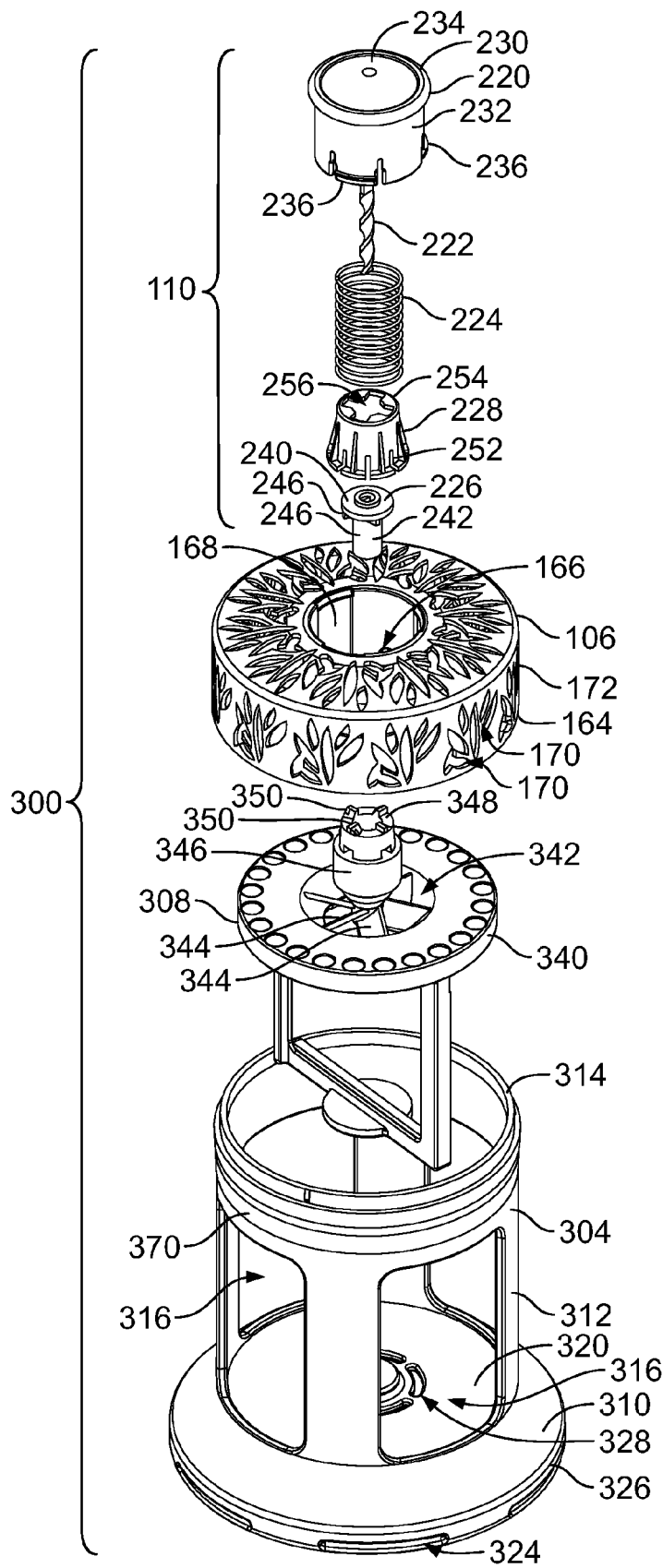
FIG. 16 is an exploded isometric view of the dispensing system of FIG. 13.
Figure 17:
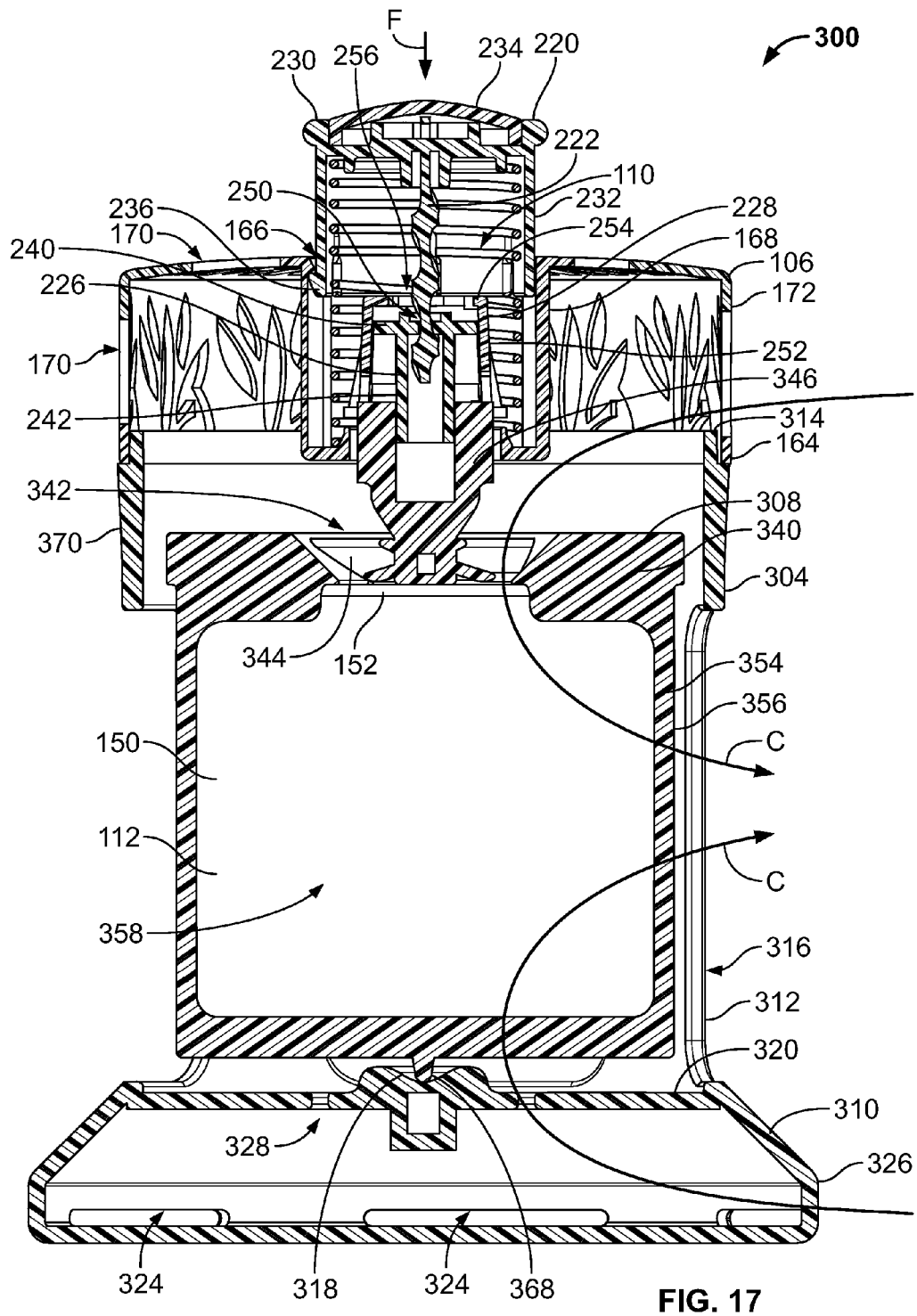
FIG. 17 is a cross-sectional view of the dispensing system of FIG. 13, taken across the line 17-17 of FIG. 13.
Figure 18:
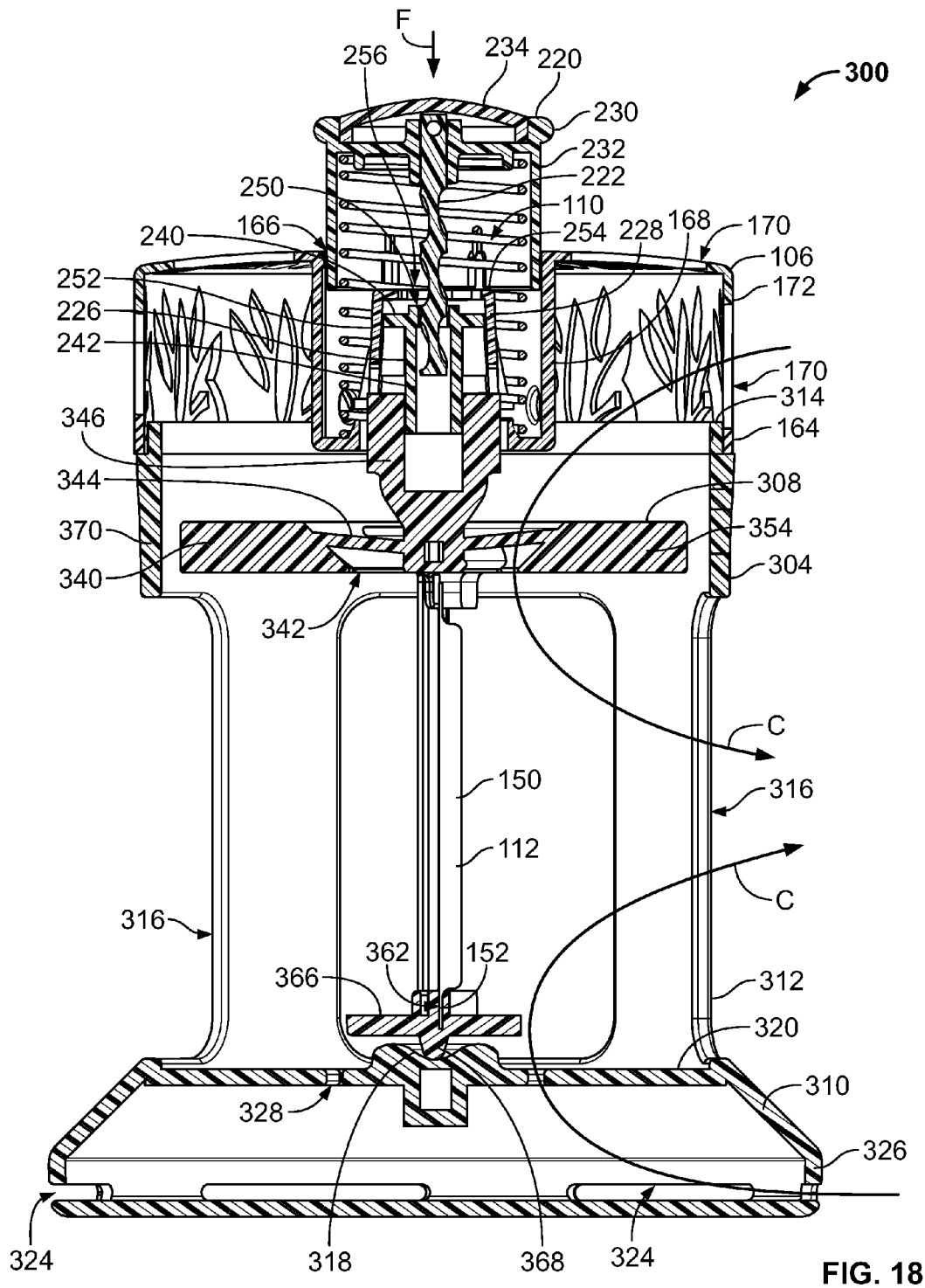
FIG. 18 is a cross-sectional view of the dispensing system of FIG. 13, taken across the line 18-18 of FIG. 13.

As shown in FIGS. 13-15, the base 304 is cylindrical in shape and includes a bottom pedestal 310 and a sidewall 312 extending upwardly therefrom to an open top end 314. A plurality of windows 316 are disposed through the sidewall 312. An opening 318 is disposed on a top side 320 of the pedestal 310 along a central longitudinal axis 322 of the dispensing system 300. In the present embodiment, the opening 318 is in the shape of a circular groove that tapers inwardly. A first set of apertures 324 is disposed around a sidewall 326 of the pedestal 310 and a second set of apertures 328 is disposed on the top side 320 of the pedestal 310 around the opening 318. The first and second sets of apertures 324, 328 on the pedestal 310 allow air to flow through the pedestal 310 and into the dispensing system 300.

Referring now to FIGS. 16-19, the fan assembly 308 includes a circular body portion 340 having an aperture 342 therethrough. A plurality of blades 344 extend into the aperture 342 and converge about or are concentric to the central longitudinal axis 322 thereof. The blades 344 are spaced to allow air to flow through the aperture 342 in the body portion 340. The fan assembly 308 includes a cylindrically shaped axle 346 that extends upwardly from the blades 344 along the central longitudinal axis 322. An upper end 348 of the axle 322 includes a plurality of teeth 350, which include sloped first sides 352A and vertical second sides 352B. A refill support 354 depends from the body 340 and is adapted to hold the refill 112. The refill support 354 includes a frame-like body 356 having an open central portion 358. A side 360 of the frame 356 is open to expose a slot 362 within the frame 356. The slot 362 is adapted to slidingly receive the flange 152 of the refill 112. Although the refill support 354 of the present embodiment includes a single slot 362 within the frame 356, it is contemplated that other retention means may be used to releasably retain the refill 112 within the fan assembly 308. Further, it is contemplated that the frame 356 may be adapted to receive a second refill 112' (not shown), e.g., by including an additional slot. A pivot is disposed on a bottom portion 366 of the frame 356 and includes a cone-shaped projection 368 depending therefrom. When assembled the cone-shaped projection 368 is adapted to rest within the opening 318 on the pedestal 310. The cone-shape projection 368 acts as a pivot point about which the fan assembly 308 rotates within the dispensing system 300.

Figure 19:
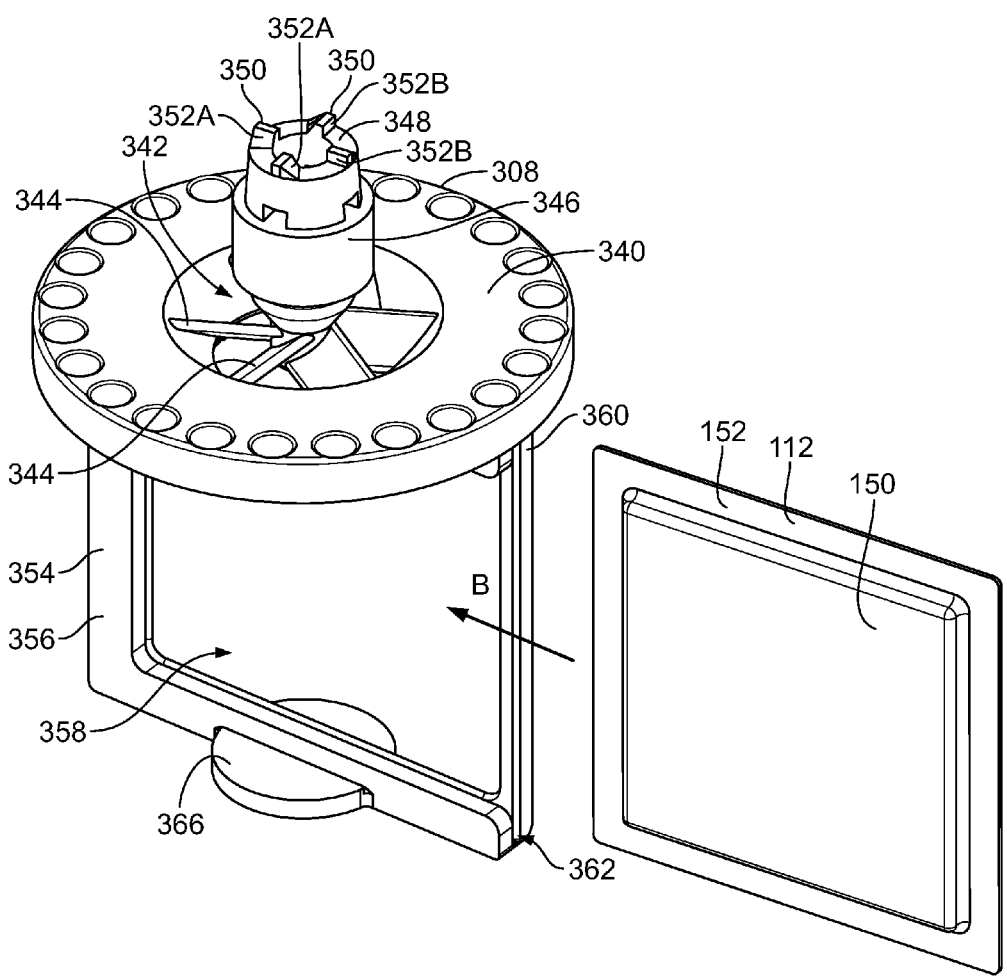
FIG. 19 is an exploded isometric view of a fan assembly and refill for use in the dispensing system of FIG. 13.

In use, the user removes the impermeable laminate 158 from the refill 112 and then slides the refill 112 into the refill support 354 of the fan assembly 308 in the direction of arrow B (See FIG. 19). The fan assembly 308, the manual drive mechanism 110, and the cover 106 are then attached to the base 304. The cover 106 frictionally engages an exterior surface 370 of the sidewall 312 of the base 304, thereby preventing the cover 106 from being released or rotated during use. In this passive state, the volatile material 156 evaporates through the permeable membrane 154 of the refill 112 and exits the dispensing system 300 through the plurality of windows 316 in the base 304 and the plurality of vents 170 in the cover 106.

At any time, a user may activate the dispensing system 300 to release a greater amount of volatile material 156 by providing the downward force F on the plunger 220 as discussed above. Application of the force F on the plunger 220 causes the screw 222 to move vertically downward through the slot 250 in the ratchet 226, which causes the ratchet 226 to rotate in a first direction. Rotation of the ratchet 226 in the first direction causes the vertical sides 248B of the ratchet teeth 246 to engage with the vertical sides 352B of the axle teeth 346, thereby causing the fan assembly 308 and attached refill 112 to rotate. The rotating fan assembly 308 and refill 112 draw air into the dispensing system 300 through the vents 170 in the cover 106, which then passes through the aperture 342 in the fan assembly 308 as indicated by arrow C. Air is also drawn into the dispensing system 300 through the first and second sets of apertures 324, 328, respectively, located in the pedestal 310. The air thereafter passes over a surface of the permeable membrane 154 of the refill 112. Subsequent to passing over the refill 112, the air is laden with the volatile material 156, which is then forced out of the dispensing system 300, by the rotating refill 112, and exits the dispensing system 300 through the plurality of windows 316. The combination of the rotating refill 112 and the plurality of windows 316 allow the air to be exhausted from the windows 316 radially about a full 360° of the dispensing system. During this active state, an increased rate and volume of the volatile material 156 is released from the dispensing system 300 as compared to the passive state During actuation of the dispensing system 300 the refill 112 rotates at least 180° about the longitudinal axis 322 of the dispensing system 300. Preferably, the refill rotates at least 360° about the longitudinal axis 322 of the dispensing system 300, and more preferably the refill makes more than one 360° rotation about the longitudinal axis 322.

When the downward force F is removed from the plunger 220, the spring 222 biases the plunger 220 upwardly to the unactuated position. The upward movement of the plunger 220 causes the upward movement of the screw 222 through the slot 250 in the ratchet 226. This upward movement causes the ratchet 226 to rotate in a second opposite direction. When the ratchet 226 rotates in the second direction, the sloped sides 248A of the ratchet teeth 246 are able to ride up and over the sloped sides 352A of the axle teeth 350, thereby allowing the ratchet 226 to rotate without causing the fan assembly 308 and refill 112 to rotate in the second opposite direction. In some embodiments, momentum created by the rotating fan assembly 308 and refill 112, will cause the fan assembly 308 and refill 112 to continue rotating in the first direction even after the force F on the plunger 220 has been removed.

The dispensing systems 100, 300 discussed above may be used with one or more refills 112, 112' having the same or different volatile material 156, 156' therein. Each refill 112, 112' initially releases a first amount M1 of volatile material at an initial point of activation, which may generally represent a mass of the volatile material released or a volume of the volatile material released. Over time the amount of the volatile material 156, 156' being released from the refills 112, 112' decreases until depletion or a residual amount of volatile material remains that is not efficacious for its intended purpose. The period of time it takes for the volatile materials 156, 156' to be depleted is represented by a lifespan T1. The lifespan T1 of the refill 112, 112' is preferably about 30 or more days, or about 60 or more days, or about 1 to about 2 weeks, or about 1 to about 4 weeks, or about 1 day to about 7 days, or about 1 day to about 30 days, or any other range.

Figure 20:
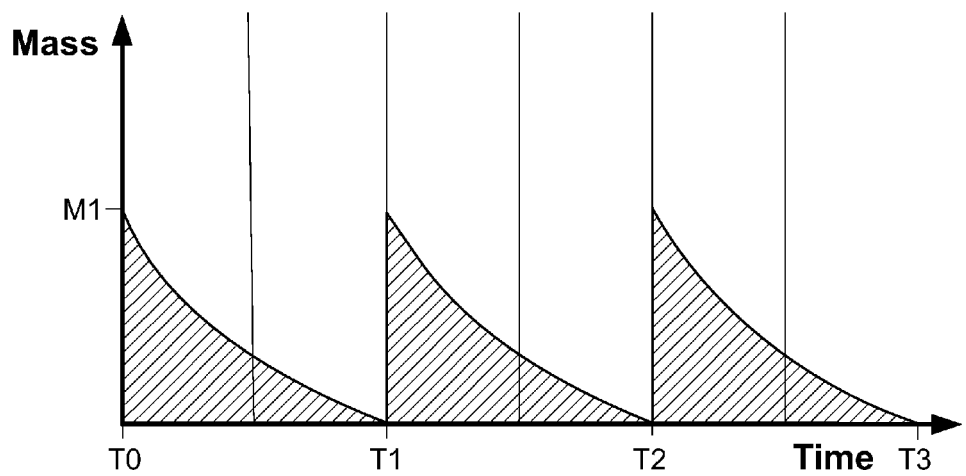
FIG. 20 is a graphical representation of a dispensing profile showing an amount of a volatile material released over time.

Referring now to FIG. 20, a first method of the refill 112 is illustrated. As shown in FIG. 20, when the refill is inserted into a dispensing system at a time 0, the refill begins releasing about M1 of volatile material. Over time the amount of volatile material being released decreases until all the volatile material is depleted at time T1. After the refill is depleted the first refill is removed and a new refill is inserted into the dispensing system. The new refill begins releasing about M1 amount of volatile material, which then decreases until the second refill is depleted at time T2.

Figure 21:
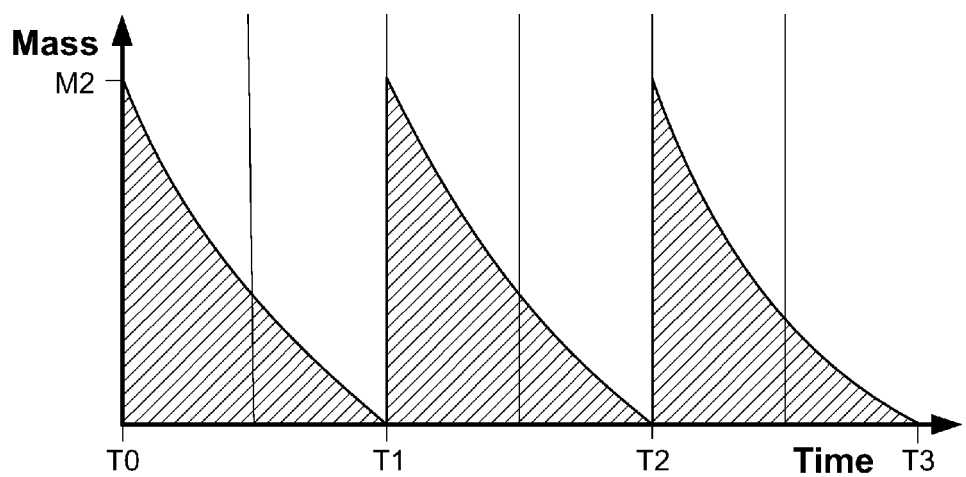
FIG. 21 is a graphical representation of a second dispensing profile showing an amount of a volatile material released over time.

As shown in FIG. 21, a second method of use is illustrated, in which two refills are inserted into the dispensing system. Inserting two refills at once increases the amount of volatile material initially being released from the dispensing system to M2. The amount of volatile material being released decreases until the refills are depleted at T1. Inserting two refills at once releases a larger initial burst of volatile material from the dispensing system, which will both be depleted at time T1.

Figure 22:
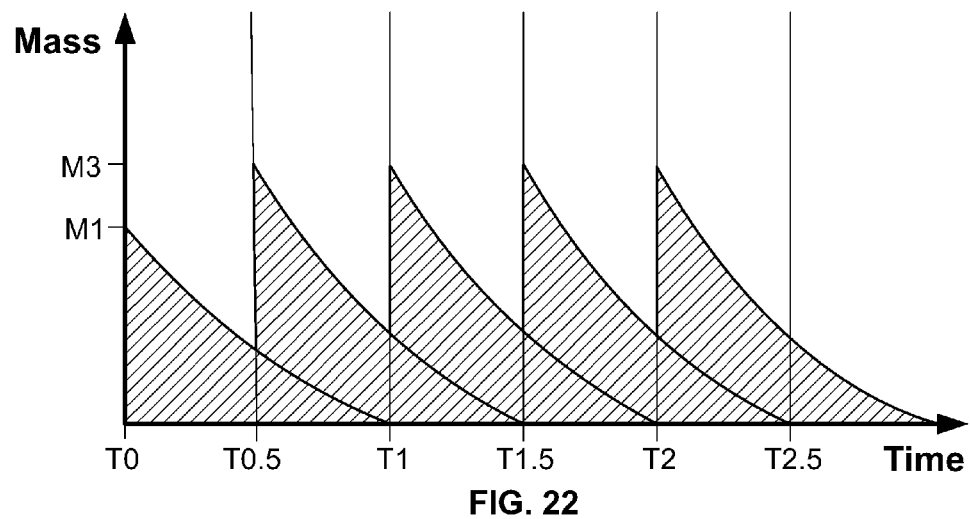
FIG. 22 is a graphical representation of another dispensing profile showing an amount of a volatile material released over time.

A third method is illustrated in FIG. 22. In this method a first refill is inserted into the dispensing system and initially releases M1 of volatile material. Part way through the lifespan of the first refill, a second refill is inserted at time T0.5. The amount of volatile material being released is M3, which is a combination of the amount of volatile material being release from the new refill in addition to the amount of volatile material still being released from the first refill. Inserting the second refill during the lifespan of the first refill allows the dispensing system to release the volatile material in a more consistent manner.

Figure 23:
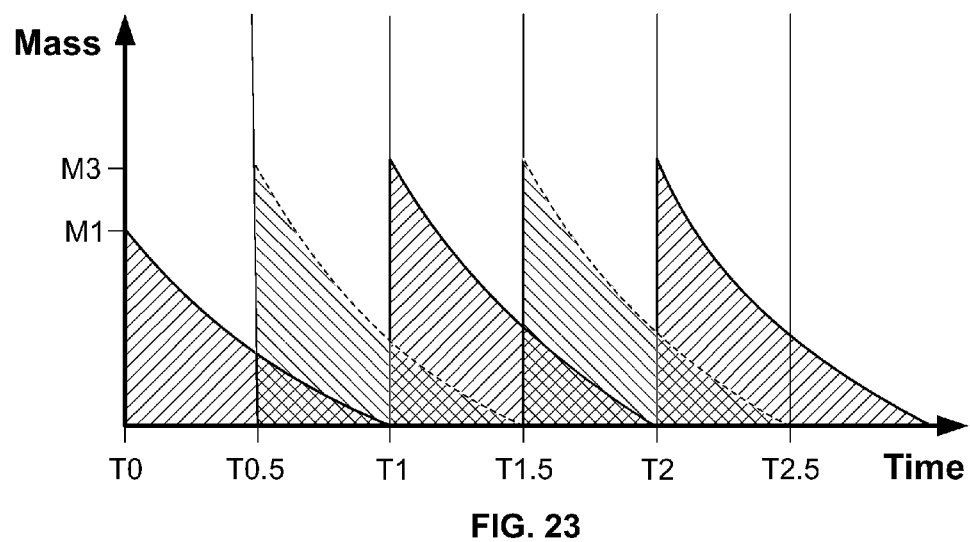
FIG. 23 is a graphical representation of a further dispensing profile showing an amount of first and second volatile materials released over time.

A fourth method is illustrated in FIG. 23, which is similar to the method shown in FIG. 22, except that the first and second refills include different volatile materials therein. The first refill having the first volatile material is inserted into the dispenser and begins releasing the first volatile material. The second refill is inserted during the lifespan of the first refill and begins to release the second volatile material. The first and second volatile materials blend to release an amount M3 of volatile material from the dispensing system. Alternating volatile materials is beneficial to prevent user habituation when the volatile materials are fragrances.

The exemplary embodiments disclosed herein are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

Other embodiments of the disclosure including all the possible different and various combinations of the individual features of each of the foregoing described embodiments and examples are specifically included herein.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A dispensing system, comprising:
a refill including a reservoir for containing a volatile material therein, wherein a permeable membrane is disposed over the reservoir and allows the volatile material to be released therethrough;
a housing adapted to retain the refill; and
a manual drive mechanism in communication with the refill,
wherein actuation of the manual drive mechanism causes the refill to rotate more than 180° about a longitudinal axis.

2. The dispensing system of claim 1, further including a fan assembly.

3. The dispensing system of claim 2, wherein the fan assembly includes a refill support for retaining the refill therein.

4. The dispensing system of claim 3, wherein the fan assembly is in communication with the drive mechanism.

5. The dispensing system of claim 1, wherein the drive mechanism is manually operated by a plunger.

6. The dispensing system of claim 5, wherein downward movement of the plunger causes a fan to rotate.

7. The dispensing system of claim 6, wherein upward movement of the plunger does not cause the fan to rotate.

8. The dispensing system of claim 1, wherein actuation of the manual drive mechanism causes the fan to rotate more than 360° about the longitudinal axis.

9. The dispensing system of claim 1, wherein the volatile material is released radially about a full 360° of the dispensing system.

10. A dispensing system, comprising:
a fan; and
a refill including a reservoir having a volatile material disposed therein, a permeable membrane covering the reservoir such that the volatile material is released through the permeable membrane in a first passive state,
wherein the fan is not concentrically disposed within the refill;
wherein rotation of the fan causes air to pass over the permeable membrane to release the volatile material in a second active state, and
wherein the volatile material is released radially about a full 360° of the dispensing system.

11. The dispensing system of claim 10 further including a drive mechanism in communication with the fan.

12. The dispensing system of claim 11, wherein the drive mechanism is manually operated by a plunger.

13. The dispensing system of claim 12, wherein downward movement of the plunger causes the fan to rotate.

14. The dispensing device of claim 13, wherein upward movement of the plunger does not cause the fan to rotate.

15. The dispensing system of claim 10 further including a second refill.

16. A dispensing system, comprising:
a non-electric drive mechanism; and
a refill having a reservoir containing a volatile material therein, the reservoir being covered by a permeable membrane,
wherein the volatile material is released from the refill in a first passive state, and
wherein the drive mechanism causes the refill to rotate more than 180° about a longitudinal axis of the dispensing system.

17. The dispensing system of claim 16, wherein the drive mechanism causes the refill to rotate more than 360° about a longitudinal axis of the dispensing system.

18. The dispensing system of claim 16, wherein the drive mechanism is manually operated by a plunger.

19. The dispensing system of claim 18, wherein downward movement of the plunger causes the refill to rotate.

20. The dispensing system of claim 16, wherein the volatile material is released radially about a full 360° of the dispensing system.

* * * * *